(12) United States Patent
Marasco et al.

(10) Patent No.: US 6,635,035 B1
(45) Date of Patent: Oct. 21, 2003

(54) TISSUE IRRIGATION ARRANGEMENT

(76) Inventors: Patrick V. Marasco, 102 Baldpate Rd., Boxford, MA (US) 01921; Donald N. Halgren, 35 Central St., Manchester, MA (US) 01944

( * ) Notice: Subject to any disclaimer, the term of this patent is extended or adjusted under 35 U.S.C. 154(b) by 163 days.

(21) Appl. No.: 09/621,636

(22) Filed: Jul. 21, 2000

Related U.S. Application Data

(63) Continuation-in-part of application No. 09/561,978, filed on May 2, 2000.
(51) Int. Cl.[7] ............................................. A61M 35/00
(52) U.S. Cl. ...................................... 604/290; 606/131
(58) Field of Search ................................ 604/290, 176, 604/289, 23, 408, 356, 319, 293; 600/21; 606/131; 128/DIG. 24, 202.12

(56) References Cited

U.S. PATENT DOCUMENTS

| | | | | |
|---|---|---|---|---|
| RE29,321 E | * | 7/1977 | Holbrook | 215/309 |
| 4,957,492 A | * | 9/1990 | McVay | 600/573 |
| 5,029,579 A | * | 7/1991 | Trammell | 128/202.12 |
| 5,312,385 A | * | 5/1994 | Greco | 604/356 |
| 5,876,387 A | * | 3/1999 | Killian et al. | 604/319 |
| 2001/0049511 A1 | * | 12/2001 | Coleman et al. | 604/290 |

* cited by examiner

Primary Examiner—Weilun Lo
Assistant Examiner—Linh Truong
(74) Attorney, Agent, or Firm—Don Halgren

(57) ABSTRACT

A method of treating a body portion wound on a patient includes the steps of arranging a flexible envelope about the wound site of the patient being treated, the envelope having at least one primary opening to permit entry of the body portion; introducing a manipulable, fluid dispersing gun through a second opening in the envelope; supplying a pressurized fluid to the gun from a fluid transfer pump; and regulating the fluid dispersed in the envelope onto the wound site by a control apparatus selected from the group comprised of a temperature control, a pressure control, a spray control, a stream control, a pulsation control, a medicament control, or a suction control.

10 Claims, 3 Drawing Sheets

TISSUE IRRIGATION ARRANGEMENT

This application is a continuation-in-part application Ser. No. 09/561,978 filed on May 2,2000.

BACKGROUND OF THE INVENTION

1. Field of the Invention

This invention relates to apparatus for washing and debriding tissue at various wound sites on the human or animal body.

2. Prior Art

Wound management is a significant portion of all medical practice today. Wounds typically occur from a burn, a contaminated trauma (blunt trauma), chronic ulceration, tendon laceration, abscess cavity to be drained, cellulitus (skin irritation), open bone fracture (compound fracture), and pressure sores. Such wounds and their treatment constitute a large percentage of the treatment provided to medical patients. The number of methods for wound cleansing and debridement have included wound cleansers such as povidone-iodine, hydrogen-peroxide, acetic acid, and chlorinated solutions which however, have cytotoxic effect on cells. Other types of wound cleaning and debridement include piston-type syringe irrigation, whirlpool treatments, wet to dry saline gauze dressings, surgical/medical debridement, enzymatic debridement, absorbent dextranomor microbeads, and pulsed lavage.

Syringe irrigation is sufficient for cleaning most simple wounds. Large complicated wounds, however, require large quantities of irrigant for effective cleansing and debridement. Whirlpool treatments are often utilized for cleansing larger wounds and appear to be common in physical therapy departments. However, with certain deep wounds flushing and debridement is difficult to achieve. The patient must often be uncomfortably positioned in order to direct jets at the wound. If a patient is incontinent, or if multiple wounds are present, cross contamination between those multiple wounds may occur. Wet to dry saline gauze dressings are simple to use and are inexpensive for the patient, but in removal of that dressing they may also damage healthy tissue and may be painful. Such dressing changes may also be a labor intensive procedure.

A relatively new procedure in wound management includes pulsed lavage wherein a pulsating water jet, is directed toward the wound site, which method is fairly effective in removing debris and bacteria from those wounds.

Pulse lavage irrigation devices typically utilize a cone shaped shield, having an open base which is placed over the wound. The shield is utilized to minimize splashing to protect the health care worker and to prevent aerosolization of body fluid. Typically a pan would be held against a lower portion of the skin of a patient being treated. A suction tube may be hung into the pan so as to drain out fluid. The fluid is typically saline or saline with an antibiotic added for wound debridement and sterilization.

A number of such physical devices are shown in the prior art to isolate and permit treatment of certain wound sites. One such device is shown in U.S. Pat. No. 5,447,504 to Baker et al. showing a misting apparatus which comprises a container secured to a limb of a patient at each end, by a rigid cuff. The cuff is held onto the limb by a securement strap and each cuff has an opening to permit an elongated listing tool to be fixedly arranged thereto. This apparatus may be satisfactory for applying a mist to a limb, for the prevention of that limb from drying out, but it has rigid conduits which puts limitations on the manipulability of the device which prevents it from applying a wide range of debriding and cleansing actions. U.S. Pat. No. 3,867,929 to Joyner et al. shows an ultrasonic treatment device in which an acoustically transparent container is wrapped around the limb containing the wound site. The container has ultrasonic transducers spaced therearound for generating acoustic vibrations through a fluid within the container and onto the wound site. This however does not provide the flushing necessary of many wound examples.

A further means for treating surface wounds is shown in U.S. Pat. No. 3,288,140 to McCarthy. This device includes cup like housings which are placed against the wound site to permit containment of the spray from a nozzle and drainage therefrom as well.

Other interesting limb treatment devices are shown in U.S. Pat. No. 3,094,983 to Macleod, U.S. Pat. No. 2,113,253 to Gray, and U.S. Pat. No. 1,105,365 to McQuhae, each showing an unusual containment for a limb to permit bathing or improve blood circulation therewithin. Each of these devices, however are unduly complicated and are not conducive to efficient personalized and adaptive treatment either at home or in the field on the wound of a patient. The prior art requires that the patients wound's conform to the apparatus, and not vice-versa.

It is thus an object of the present invention, to overcome the shortcomings of the prior art.

It is a further object of the present invention, to provide a wound treatment arrangement comprising a self-contained environment around the wound site, which is safe both for the medical practitioner and for the patient.

It is yet a further object of the present invention to provide a wound treatment apparatus which is efficient in its delivery of treatment and efficient in its containment of contaminants.

It is still yet a further object of the present invention to provide a wound treatment apparatus which minimizes possibilities of contamination and maximizes the effectiveness of the irrigation being utilized therewith.Brief

SUMMARY OF THE INVENTION

The present invention comprises an apparatus for the washing and debridement of wounds on limbs and body portions of patients. Such apparatus may be utilized outside of a formal medical facility, and for use in a place such as the home or in the field. It is the intent of this invention to replace or minimize the use of a whirlpool bath, to eliminate cross-contamination of body fluids, and to minimize the spread of bacteria, hepatitis and other staff and pathogenic organisms.

The present invention comprises a flexible envelope of transparent plastic material having a first primary opening for receipt of a body limb or for attachment to a body portion having a wound site thereon. The envelope will include at least one secondary opening having a flexible support collar therearound for insertion of a fluid delivery device. The fluid delivery device may comprise a hand manipulable gun for the delivery of fluid under pressure. The fluid may be a gas and/or fluid mixture. The gas proposed may comprise oxygen or carbon dioxide or hydrogen peroxide useful for sterilization purposes. The flexible envelope covering the wound should contain at least one tertiary port for the drainage and withdrawal of fluid, washed away tissue, and for the release of pressurized gas which has been delivered into the envelope.

In a first preferred embodiment of the present invention, the flexible transparent envelope comprises a bag-like structure having an enlarged central portion with a tapered sealable or securable strap or band disposed adjacent to periphery of the opening at the narrow end. This permits the distal end of an arm or foot to be inserted within the bag for debridement of a wound therein. The invention also includes a pressurized source of fluid which fluid may be a saline solution and a gas such as carbon dioxide or oxygen or the like, supplied by a hand manipulable pressurized gun, the gun fitting in the access port in a snug fitting relation, the access port having the collar which collar may be stretchably elasticized, meeting with the chamber of the gun so as to minimize or eliminate any loss of pressure or fluid from within the envelope. The containment envelope may have a drainage port disposed through the envelope at a position generally diametrically opposed to the access port therein. The drainage port has a conduit which is in fluid communication with a disposable collection bag or a suction line.

In a preferred embodiment of the present invention, the disposable bag itself is in communication with a suction line with the fluid delivery source. The fluid delivery source in this embodiment comprises a drivable motor having an elongated rotor shaft. At one first end of the rotor shaft there is a pump arranged thereon, to provide fluid pressure to the hand manipulable gun. The fluid under pressure as aforementioned, may be a saline solution, a blend of gas and fluid medicaments, any or all of which may be heated or cooled to effect the desired treatment upon the patients body component within the enclosure bag. The other or second end of the rotatable shaft of the motor within the fluid source is attached to a suction pump within the housing thereof. The suction pump may be in fluid communication with the disposable collection bag to provide a vacuum incentive for drainage of fluids within the patient enclosure bag. In this embodiment, a common empowered motor with an extended shaft, provides drive means for both a pressure pump and a vacuum source so as to effect a continuous feed of and withdrawal of fluid onto the patient's wound treatment site and removal of that fluid simultaneously therewith after that fluid has treated the patient's body portion.

In a further embodiment of the present invention, the pressurized pump may be of a pulsating nature, having a rotating wheel arrangement spinning within a sinusoidal inner surface, squeezing a flexible fluid feedline therebetween. The feedline having a pickup end at a fluid source and a fluid discharge end at the hand manipulable gun. Rotation of the wheel within the sinusoidal surface effects intermittent pulses to be generated and discharged from the pressure feedline.

Another further embodiment of the pulsed pressurized fluid feed system may comprise an intermittent arcuate segment spaced by an intermittent arcuate opening, wherein a rotating pair of wheels presses a flexible feed tube against an arcuate segment and pressure is released within the feed tube during the wheels respective passage over the arcuate void to effect the pulsed pressurized fluid being fed to the hand manipulable gun directed within the patient enclosure bag.

In a further embodiment of the present invention, the suction side of the pressure fluid generating apparatus may also be effected in a pulsed manner similar to the fluid pressure side thereof. The suction or vacuum side of the apparatus may be in-phase or out-of-phase with the fluid pressure generation side of the fluid delivery apparatus.

In yet a still further object of the present invention, the flexible patient portion containing envelope has a directly attached sump for the collection of fluid which has been sprayed upon the patient's wound site. The sump portion of the flexible envelope may be unitary therewith or may be removable or separable from the flexible patient-enclosure portion thereof, yet attached thereto and having a one-way valve therebetween such a duck-bill type valve arranged therebetween.

Thus, what has been shown is a unique irrigation arrangement for treating a wound site of a patient, while providing a self-contained environment for the patient and safety for the medical practitioner while also providing containment of possibly hazardous biological fluids therefrom. The system promotes efficiency in one preferred embodiment, by effecting pressure and suction simultaneously from a common source within the apparatus.

The invention thus comprises a method of treating a body portion wound on a patient comprising the steps of: arranging a flexible envelope about the wound site of the patient being treated, the envelope having at least one primary opening to permit entry of the body portion; introducing a manipulable, fluid dispersing gun through a second opening in the envelope; supplying a pressurized fluid to the gun from a fluid transfer pump; and regulating the fluid dispersed in the envelope onto the wound site by a control apparatus selected from the group comprised of a temperature control, a pressure control, a spray control, a stream control, a pulsation control, a medicament control, or a suction control. The method includes collecting the fluid dispersed onto the wound site, in a separate collection bag; collecting the fluid dispersed onto the wound sites in a sump collection bag attached directly to the envelope; collecting and filtering the fluid sprayed into the envelope to permit the wound site tissue to be sampled; pumping the fluid into the envelope while simultaneously suctioning the fluid from the envelope; pumping and suctioning the fluid by a common fluid transfer apparatus; abrading the wound site by a bristle attached to the nozzle on the gun; attaching a pressure pump and suction pump onto a common shaft of a motor to effect the simultaneous pumping and suctioning of fluid with respect to the envelope.

BRIEF DESCRIPTION OF THE DRAWINGS

The objects and advantages of the present invention will become more apparent when viewed in conjunction with the following drawings in which.

DESCRIPTION OF THE PREFERRED EMBODIMENTS

Figure 1:
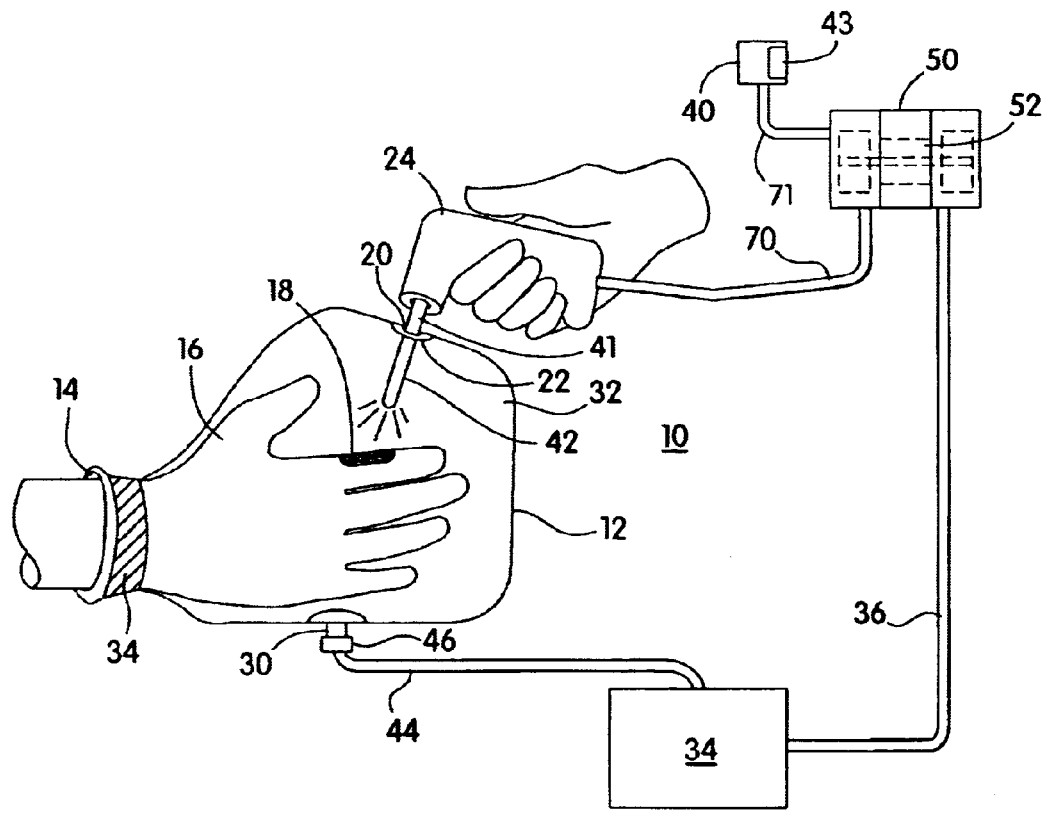
FIG. 1 is a side elevational view of a wound treatment shield and pressurized fluid arrangement constructed according to the principles of the present invention, shown utilized on a body part wound.

Referring now to the drawings in detail, and particularly to FIG. 1, there is shown the present invention which comprises an apparatus 10 for the washing and debridement of wounds on limbs and body portions of patients. Such apparatus 10 may be utilized outside of a formal medical facility, and for use in a place such as the home or in the field. It is the intent of this invention to replace or minimize the use of a whirlpool bath, to eliminate cross-contamination of body fluids, and to minimize the spread of bacteria, hepatitis and other staff and pathogenic organisms.

The present invention includes a flexible envelope 12 of transparent plastic material having a first primary opening 14 for receipt of a body limb 16 or for attachment to a body portion having a wound site 18 thereon. The envelope 12 will include at least one secondary opening 20 having a flexible support collar 22 therearound for insertion of a fluid delivery device 24. The fluid delivery device 24 may comprise a hand manipulable gun for the delivery of fluid under pressure. The fluid may be a gas and/or liquid mixture. The gas proposed may comprise oxygen or carbon dioxide or hydrogen peroxide useful for sterilization purposes. The flexible envelope 12 covering the wound 18 should contain at least one tertiary port 30 for the drainage and withdrawal of fluid, washed-away tissue, and for the release of pressurized gas which has been delivered into the envelope 12.

In a first preferred embodiment of the present invention, the flexible transparent envelope 12 comprises a bag-like structure having an enlarged central portion 32 with a tapered sealable or securable strap or band 34 disposed adjacent to periphery of the opening 14 at the narrow end. This permits the distal end of an arm or foot to be inserted within the bag for debridement of a wound therein. The invention also includes a pressurized source of fluid 40 which fluid may be for example, a saline solution and a gas for example, such as carbon dioxide or oxygen or the like, supplied to the a hand manipulable pressurized gun 24, the gun 24 fitting in the access port 20 in a snug fitting relation, the access port opening 20 having the collar 22 which collar 22 may be stretchably elasticized, meeting with the barrel 41 of the gun 24 so as to minimize or eliminate any loss of pressure or fluid from within the envelope 12. A nozzle 42 may be arranged on the distal end of the barrel 41 of the gun 24. The nozzle 42 may be adjustable as by rotation similar to a garden hose nozzle, to effect a straight stream or a spread out spray. The nozzle 42 may also have a sponge or short bristles thereon, (not shown for clarity) to permit the wound 18 to be manually abraded during the fluid debridement process. The containment envelope 12 may have a drainage port 30 disposed through the envelope at position generally diametrically opposed to the access port 20 therein. The drainage port 30 in this embodiment, has a conduit 44 which is in fluid communication with a disposable collection bag 34 or a suction line 36. A tissue residue filter 46 may be removably disposed within the drainage port 30 or in the conduit 44, to permit biological sampling of the material take from the wound site 18.

Figure 3:
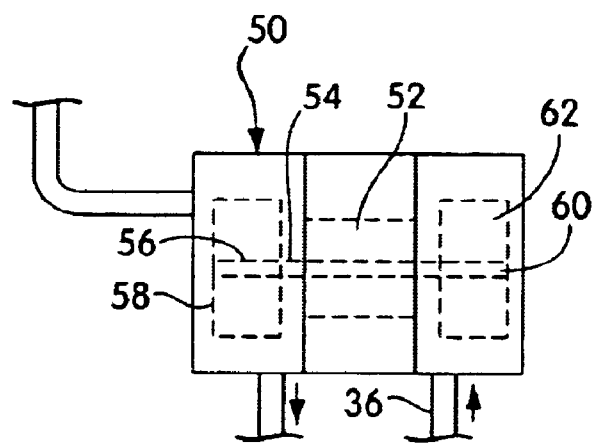
FIG. 3 is a representation of the pressure and suction generating apparatus of the present invention.

In another preferred embodiment of the present invention, the disposable bag 12 itself is in communication with a suction line 36 with the fluid transfer pump 50. The fluid transfer pump 50, as shown in FIGS. 1 and 3 in this embodiment comprises a drivable motor. 52 having an elongated rotor shaft 54. At one first end 56 of the rotor shaft 54 there is a fluid pressure generating pump 58 arranged thereon, to provide fluid pressure to the hand manipulable gun 24, from the source/reservoir 40. The fluid under pressure as aforementioned, may be a saline solution, a blend of gas and fluid medicaments, any or all of which may be heated/cooled/treated by a heater/chiller/treater 43 within the source/reservoir 40, to effect the treatment upon the patients body component 16 within the enclosure bag 12. The other or second end 60 of the rotatable shaft of the motor within the fluid transfer pump 50 is attached to a suction pump 62 within the housing. thereof. The suction pump 62 may be in fluid communication with the disposable collection bag 34, to provide a vacuum incentive for drainage of fluids within the patient enclosure bag 34. In this embodiment, a common empowered motor 52 with an extended shaft 54, thus provides drive means for both a pressure pump 58 and a vacuum source 62 so as to effect a dual continuous feed of and withdrawal of fluid onto the patient's wound treatment site and removal of that fluid simultaneously therewith after that fluid has treated the patient's body portion.

Figure 4:
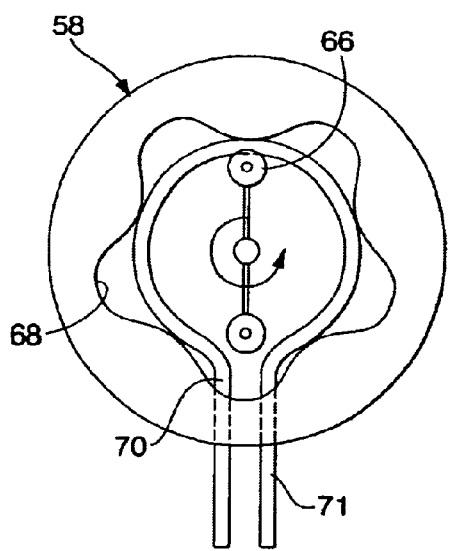
FIG. 4 is a side elevational view of a pulse-generating mechanism for the fluid pressure generating apparatus.

In a still further embodiment of the present invention, the pressurized pump 58 may be of a pulsating nature, having a rotating wheel 66 arranged spinning within a sinusoidal inner surface 68, squeezing a flexible fluid feedline 70 therebetween, as may be seen in FIG. 4. The feedline 70 having a pickup end 71 at a fluid source 40 and a fluid discharge end at the hand manipulable gun 24. Rotation of the wheel 66 within the sinusoidal surface 68 effects intermittent pulses to be generated and discharged through the pressure, feedline 70 and out through the nozzle 42 of the gun 24.

Figure 5:
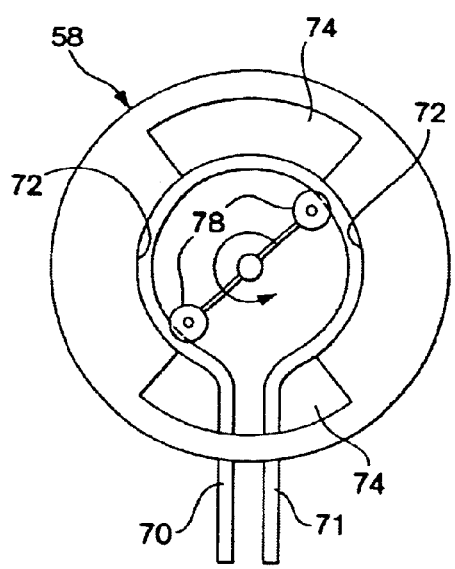
FIG. 5 is a side elevational view of a further embodiment of the pulse-generation apparatus as shown in FIG. 4.

Another further embodiment of the pulsed pressurized fluid feed pump 58 may be comprised an intermittent arcuate segment 72 spaced by an intermittent arcuate opening 74 within a hub 76, as shown in FIG. 5, wherein a rotating pair of wheels 78 presses a flexible feed tube against an arcuate segment 72 and pressure is released within the feed tube 70 during the wheels 78 respective passage over the arcuate void 74 to effect the pulsed pressurized fluid being fed to the hand manipulable gun 24 directed within the patient enclosure bag 12.

In yet another further embodiment of the present invention, the suction side of the pressure fluid generating apparatus may also be effected in a pulsed manner similar to the fluid pressure side thereof, as shown in FIGS. 4 and 5. The suction or vacuum side 62 of the apparatus 50 may be in-phase or out-of-phase with the fluid pressure generation side 58 of the fluid transfer pump 50.

Figure 2:
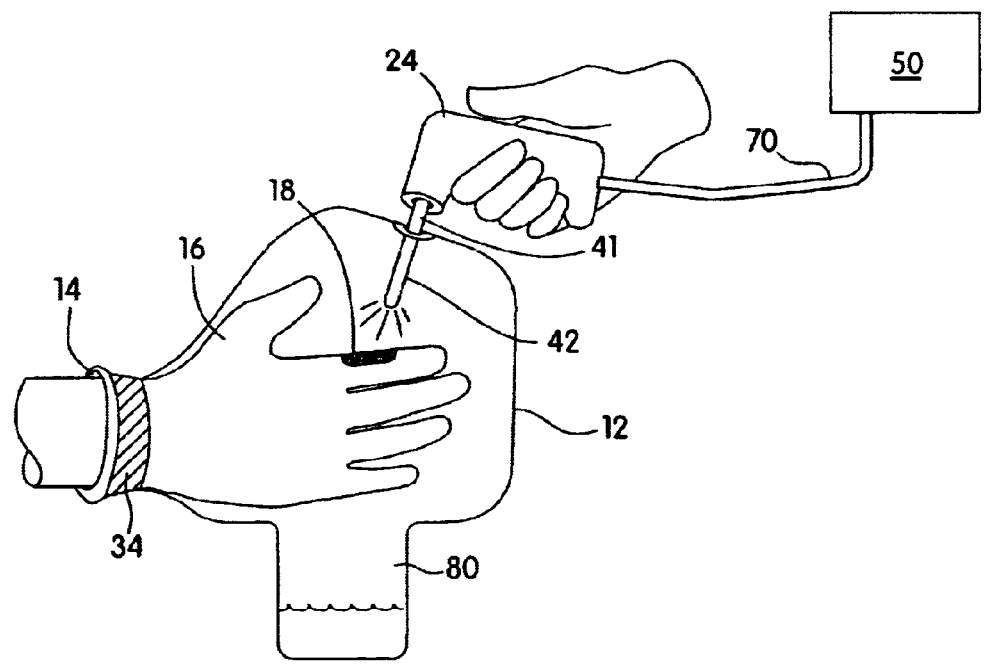
FIG. 2 is a side elevational view of the wound treatment containment apparatus of the present invention in a further embodiment thereof.
Figure 6:
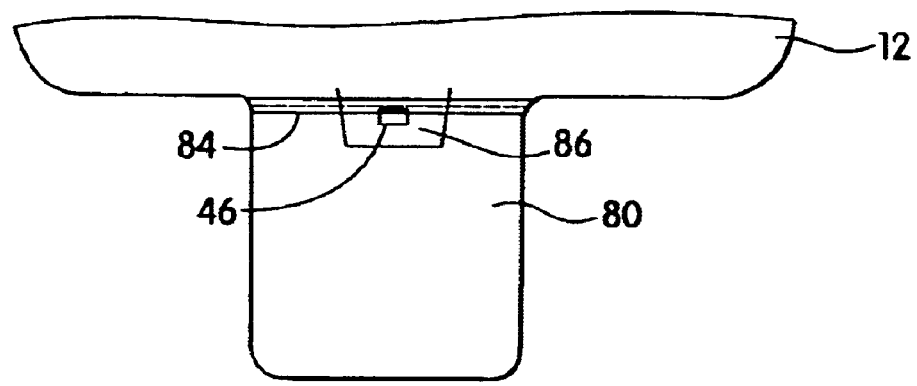
FIG. 6 is a side elevational view of a further embodiment of the fluid collection apparatus arranged in conjunction with the flexible body-portion enclosing envelope.

In yet a still further object of the present invention, the flexible patient portion containing envelope 12 has a directly attached sump 80 for the collection of fluid which has been sprayed upon the patient's wound site 18. The sump portion 80 of the flexible envelope 12 may be unitary therewith, as shown in FIG. 2. Alternatively, the sump 80 may be removable or separable from the flexible, patient-enclosure portion thereof, yet attached thereto by a multiple re-sealable seam 84 arranged to seal the envelope. 12 and the collection bag 80. The juncture between the envelope 12 and bag 80 may have a one-way valve 86 therebetween such as a duck-bill type valve arranged therebetween, as shown in FIG. 6 to prevent back flow. The filter 46 may also be arranged within the throat of the valve 86 to permit sampling of tissue thereat.

Thus, what has been shown is a unique irrigation arrangement for treating a wound site of a patient, while providing a self-contained environment for the patient and safety for the medical practitioner while also providing containment of possibly hazardous biological fluids therefrom. The system promotes efficiency in one preferred embodiment, by effecting pressure and suction simultaneously from a common source within the apparatus.

We claim:

1. A method of treating a body portion wound on a patient comprising the steps of:
   arranging a flexible envelope about the wound site of the patient being treated, said envelope having at least one primary opening to permit entry of said body portion;
   introducing a manipulable, fluid dispersing gun through a second opening in said envelope;
   supplying a pressurized fluid to said gun from a fluid transfer pump;
   regulating said fluid dispersed in said envelope onto said wound site by a control apparatus selected from the group comprised of a temperature control, a pressure control, a spray control, a stream control, a pulsation control, a medicament control, or a suction control;
   maintaining said envelope on the patient's wound site in an expanded configuration; and
   collecting and filtering said fluid sprayed into said envelope to permit said wound site tissue to be sampled.

2. The method as recited in claim 1, including the step of:
   collecting said fluid dispersed onto said wound site in a separate collection bag.

3. The method as recited in claim 1, including the step of:
   collecting said fluid dispersed onto said wound site in a sump collection bag attached directly to said envelope.

4. The method as recited in claim 1, including the step of:
   pumping said fluid into said envelope while simultaneously suctioning said fluid from said envelope.

5. The method as recited in claim 4, including the step of:
   pumping and suctioning said fluid by a common fluid transfer apparatus.

6. The method as recited in claim 1, including the step of:
   abrading said wound site by a bristle attached to said nozzle on said gun.

7. The method as recited in claim 4, including the step of:
   attaching a pressure pump and suction pump onto a common shaft of a motor to effect said simultaneous pumping and suctioning of fluid with respect to said envelope.

8. A method of treating a body portion wound with a fluid treatment onto a patient comprising the steps of:
   arranging a flexible envelope about the wound site of the patient being treated, said envelope having at least one primary opening to permit entry of said body portion;
   sealing said envelope about said patient's wound site;
   introducing a nozzle of a manipulable, fluid dispersing gun through a second opening in said envelope;
   supplying a pressurized fluid to said gun from a fluid transfer pump;
   treating said wound with said dispersed fluid;
   disposing of said nozzle of said gun after said fluid treatment has been completed on the patient; and
   collecting and filtering said fluid dispersed into said envelope to permit said wound site tissue to be sampled.

9. The method as recited in claim 8, including the step of:
   maintaining said envelope on the patient's wound site in an expanded configuration after said fluid treatment.

10. The method as recited in claim 8, including the step of:
    regulating said fluid dispersed in said envelope onto said wound site by a control apparatus selected from the group comprised of a temperature control, a pressure control, a spray control, a stream control, a pulsation control, a medicament control, or a suction control.

* * * * *